United States Patent
Lin et al.

(10) Patent No.: US 10,507,246 B2
(45) Date of Patent: Dec. 17, 2019

(54) TDNS-AS1411-NUCLEIC ACID DRUG NANOCOMPOSITE BASED DRUG DELIVERY SYSTEM AND PREPARATION METHOD THEREOF

(71) Applicant: Sichuan University, Chengdu (CN)

(72) Inventors: Yunfeng Lin, Chengdu (CN); Sirong Shi, Yibin (CN); Xiaoxiao Cai, Chengdu (CN); Shiyu Lin, Ruian (CN); Qianshun LI, Chengdu (CN)

(73) Assignee: Sichuan University, Chengdu (CN)

( * ) Notice: Subject to any disclaimer, the term of this patent is extended or adjusted under 35 U.S.C. 154(b) by 41 days.

(21) Appl. No.: 15/555,380

(22) PCT Filed: Nov. 21, 2016

(86) PCT No.: PCT/CN2016/106627
§ 371 (c)(1),
(2) Date: Sep. 1, 2017

(87) PCT Pub. No.: WO2018/082126
PCT Pub. Date: May 11, 2018

(65) Prior Publication Data
US 2018/0344863 A1  Dec. 6, 2018

(30) Foreign Application Priority Data
Nov. 2, 2016  (CN) .......................... 2016 1 0940890

(51) Int. Cl.
*A61K 47/54* (2017.01)
*C12N 15/115* (2010.01)
*A61K 31/7088* (2006.01)

(52) U.S. Cl.
CPC ........ *A61K 47/549* (2017.08); *A61K 31/7088* (2013.01); *C12N 15/115* (2013.01); *C12N 2310/16* (2013.01); *C12N 2310/3519* (2013.01); *C12N 2320/32* (2013.01)

(58) Field of Classification Search
CPC ............. A61K 31/711; A61K 2300/00; A61K 47/6929; C12N 15/115; C12N 2310/16; C12N 2320/32
USPC ...... 424/9.1; 435/6.1, 91.1, 81.31, 455, 458; 514/44; 536/23.1, 24.5
See application file for complete search history.

(56) References Cited

FOREIGN PATENT DOCUMENTS

| CN | 104645338 A | 5/2015 |
|---|---|---|
| CN | 104774857 A | 7/2015 |
| CN | 104784703 A | 7/2015 |
| CN | 105296491 A | 2/2016 |
| CN | 105366730 A | 3/2016 |

OTHER PUBLICATIONS

Charoenphol et al. (Molecular Pharmaceutics, vol. 5, No. 11, pp. 1721-1725 (2014)), (Year: 2014).*
Xu et al (Nanoscale Res. Letters, vol. 11, p. 437, pp. 1-8 (2016)). (Year: 2016).*
Li et al (ACS Nano, vol. 5, No. 11, pp. 8783-8789 (2011)). (Year: 2011).*
Li, Jiang et al., Self-Assembled Multivalent DNA Nanostructures for Noninvasive Intracellular Delivery of Immunostimulatory CpG Oligonucleotides. ACSNANO Oct. 11, 2011 (Oct. 11, 2011) No. 11, vol. 5, pp. 8783-8789.
Phapanin, Charoenphol et al., Aptamer-Targeted DNA Nanostructures for Therapeutic Delivery. Molecular Pharmaceutics Apr. 16, 2014(Apr. 16, 2014), No. 5, vol. 11, pp. 1721-1725.
Xu, Xiao Bo et al., G4-Tetra DNA Duplex Induce Lung Cancer Cell Apoptosis in A549 Cells. Nanoscale Research Letters Oct. 1, 2016 (Oct. 1, 2016), vol. 11, pp. 1-8.
Dong, Shibiao, et al., The DNA Tetrahedron Nanostructure Materials and Their Applications. Progress in Chemistry, Aug. 25, 2015, No. 9, vol. 27, pp. 1191-1197.

\* cited by examiner

*Primary Examiner* — Jane J Zara
(74) *Attorney, Agent, or Firm* — Gokalp Bayramoglu

(57) ABSTRACT

This invention discloses a method for preparing TDNs-AS1411-nucleic acid drug nanocomposite based drug delivery system, which includes the following steps: binding AS1411 and nucleic acid drug to a tetrahedral DNA nanostructure respectively; selecting four DNA single strands that respectively carry AS1411 and nucleic acid drug; mixing the four DNA single strands; mixing the DNA single strands and the TM buffer uniformly; putting the mixture into a PCR apparatus; raising the temperature to 95° C. quickly and maintaining for 10 min; and next cooling down to 4° C. and maintaining for 20 min to obtain the TDNs-AS1411-nucleic acid drug nanocomposite based drug delivery system. This drug delivery system can directly act on cell nucleus and will not be degraded by lysosomal. The targeting specificity is good. The drug can take a good efficacy and the pertinency is high.

13 Claims, No Drawings
Specification includes a Sequence Listing.

SEQUENCE LISTING

<160> NUMBER OF SEQ ID NOS: 13

<210> SEQ ID NO 1
<211> LENGTH: 63
<212> TYPE: DNA
<213> ORGANISM: Artificial Sequence
<220> FEATURE:
<223> OTHER INFORMATION: The sequence is synthesized.

<400> SEQUENCE: 1
atttatcacc cgccatagta gacgtatcac caggcagttg agacgaacat tcctaagtct      60
gaa                                                                   63

<210> SEQ ID NO 2
<211> LENGTH: 63
<212> TYPE: DNA
<213> ORGANISM: Artificial Sequence
<220> FEATURE:
<223> OTHER INFORMATION: The sequence is synthesized.

<400> SEQUENCE: 2
acatgcgagg gtccaatacc gacgattaca gcttgctaca cgattcagac ttaggaatgt    60
tcg    63

<210> SEQ ID NO 3
<211> LENGTH: 63
<212> TYPE: DNA
<213> ORGANISM: Artificial Sequence
<220> FEATURE:
<223> OTHER INFORMATION: The sequence is synthesized.

<400> SEQUENCE: 3
actactatgg cgggtgataa aacgtgtagc aagctgtaat cgacgggaag agcatgccca    60
tcc    63

<210> SEQ ID NO 4
<211> LENGTH: 63
<212> TYPE: DNA
<213> ORGANISM: Artificial Sequence
<220> FEATURE:
<223> OTHER INFORMATION: The sequence is synthesized.

<400> SEQUENCE: 4
acggtattgg accctcgcat gactcaactg cctggtgata cgaggatggg catgctcttc    60
ccg    63

<210> SEQ ID NO 5
<211> LENGTH: 90
<212> TYPE: DNA
<213> ORGANISM: Artificial Sequence
<220> FEATURE:
<223> OTHER INFORMATION: The sequence is synthesized.

<400> SEQUENCE: 5
ggtggtggtg gttgtggtgg tggtggtatt tatcacccgc catagtagac gtatcaccag    60
gcagttgaga cgaacattcc taagtctgaa    90

<210> SEQ ID NO 6
<211> LENGTH: 90
<212> TYPE: DNA
<213> ORGANISM: Artificial Sequence
<220> FEATURE:
<223> OTHER INFORMATION: The sequence is synthesized.

<400> SEQUENCE: 6
ggtggtggtg gttgtggtgg tggtggtaca tgcgagggtc caataccgac gattacagct    60
tgctacacga ttcagactta ggaatgttcg    90

<210> SEQ ID NO 7
<211> LENGTH: 90
<212> TYPE: DNA
<213> ORGANISM: Artificial Sequence
<220> FEATURE:
<223> OTHER INFORMATION: The sequence is synthesized.

<400> SEQUENCE: 7
ggtggtggtg gttgtggtgg tggtggtact actatggcgg gtgataaaac gtgtagcaag    60
ctgtaatcga cgggaagagc atgcccatcc    90

<210> SEQ ID NO 8
<211> LENGTH: 90
<212> TYPE: DNA
<213> ORGANISM: Artificial Sequence
<220> FEATURE:
<223> OTHER INFORMATION: The sequence is synthesized.

<400> SEQUENCE: 8
ggtggtggtg gttgtggtgg tggtggtacg gtattggacc ctcgcatgac tcaactgcct    60
ggtgatacga ggatgggcat gctcttcccg    90

<210> SEQ ID NO 9
<211> LENGTH: 81
<212> TYPE: DNA
<213> ORGANISM: Artificial Sequence
<220> FEATURE:
<223> OTHER INFORMATION: The sequence is synthesized.

<400> SEQUENCE: 9
tccatgacgt tcctgacgat ttatcacccg ccatagtaga cgtatcacca ggcagttgag    60
acgaacattc ctaagtctga a    81

<210> SEQ ID NO 10
<211> LENGTH: 81
<212> TYPE: DNA
<213> ORGANISM: Artificial Sequence
<220> FEATURE:
<223> OTHER INFORMATION: The sequence is synthesized.

<400> SEQUENCE: 10
tccatgacgt tcctgacgac atgcgagggt ccaataccga cgattacagc ttgctacacg    60
attcagactt aggaatgttc g    81

<210> SEQ ID NO 11
<211> LENGTH: 81
<212> TYPE: DNA
<213> ORGANISM: Artificial Sequence
<220> FEATURE:
<223> OTHER INFORMATION: The sequence is synthesized.

<400> SEQUENCE: 11
tccatgacgt tcctgacgac tactatggcg ggtgataaaa cgtgtagcaa gctgtaatcg    60
acgggaagag catgcccatc c    81

<210> SEQ ID NO 12
<211> LENGTH: 81
<212> TYPE: DNA
<213> ORGANISM: Artificial Sequence
<220> FEATURE:
<223> OTHER INFORMATION: The sequence is synthesized.

<400> SEQUENCE: 12
tccatgacgt tcctgacgac ggtattggac cctcgcatga ctcaactgcc tggtgatacg    60
aggatgggca tgctcttccc g    81

<210> SEQ ID NO 13
<211> LENGTH: 18
<212> TYPE: DNA
<213> ORGANISM: Artificial Sequence
<220> FEATURE:
<223> OTHER INFORMATION: The sequence is synthesized.

```
<400> SEQUENCE: 13
tccatgacgt tcctgacg                                                    18
```

US 10,507,246 B2

TDNS-AS1411-NUCLEIC ACID DRUG NANOCOMPOSITE BASED DRUG DELIVERY SYSTEM AND PREPARATION METHOD THEREOF

CROSS REFERENCE TO RELATED APPLICATIONS

This application is the national phase entry of International Application No. PCT/CN2016/106627, filed on Nov. 21, 2016, which is based upon and claims priority to Chinese Patent Application No. CN2016109408903, filed on Nov. 2, 2016, the entire contents of which are incorporated herein by reference.

TECHNICAL FIELD

The invention relates to the field of bio-medical technology, specifically relates to a TDNs-AS1411-nucleic acid drug nanocomposite based drug delivery system and preparation method thereof.

BACKGROUND

Tetrahedral DNA nanostructures (TDNs) is the self-assembly product based on DNA nanotechnology. Due to its advantages of simple synthesis method, high yield, stable structure, excellent mechanical properties and rich molecular modification sites, it is widely studied and applied in molecular diagnosis, bioimaging, molecular delivery and targeted drug delivery, etc. Compared to most of the traditional nano materials, TDNs can be transported to cell lysosomes through caveolin-mediated endocytosis pathway and microtubule-dependent pathway and can maintain the structure in cells for a long time. It has been reported that the TDNs can successfully transport the immunostimulant CpG into cells to take effect. However, as with the individual TDNs, the drugs are also carried into the lysosomes, which lead to the rapid degradation of drugs by lysosomes.

Nucleic acid aptamer AS1411 is a single-strand DNA that can specifically bind to pyrenin. Pyrenin is highly expressed on nucleus and the surface of the tumor cell membrane. Moreover, the AS1411 can be mediated into nucleus by pyrenin to inhibit the DNA replication, so as to force the cells to stay in S phase, thereby inhibiting cell proliferation. Meanwhile, AS1411 interferes the binding of pyrenin and bcl-2 so as to promote apoptosis of cells. Hence, AS1411 has a great prospect in cancer diagnosis and treatment.

However, the TDNs and AS1411 in combination with nucleic acid drugs for preparing a drug delivery system has not been reported yet.

SUMMARY OF THE INVENTION

In view of the above deficiencies in the prior art, this invention provides a TDNs-AS1411-nucleic acid drug nanocomposite based drug delivery system and preparation method thereof. Thus, a new drug delivery system is provided. Also, the problem that drugs delivered by the drug delivery system are susceptible to degradation by lysosomes, is effectively solved.

In order to achieve the above objective, the technical solutions of this invention to solve the technical problem are as below:

A method for preparing TDNs-AS1411-nucleic acid drug nanocomposite based drug delivery system includes the following steps:

binding AS1411 and nucleic acid drug to a tetrahedral DNA nanostructure respectively;

selecting four DNA single strands that respectively carry AS1411 and nucleic acid drug;

mixing the four DNA single strands;

adding the DNA single strands to TM buffer;

mixing the DNA single strands and the TM buffer uniformly;

putting the mixture into a PCR apparatus;

raising the temperature to 95° C. quickly and maintaining for 10 min; and next, cooling down to 4° C. and maintaining for 20 min to obtain the TDNs-AS1411-nucleic acid drug nanocomposite based drug delivery system.

Further, the TM buffer with pH value of 8.0, includes 5-10 mM Tris-HCl and 5-50 mM $MgCl_2$.

Further, the TM buffer with pH value of 8.0, includes 10 mM Tris-HCl and 50 mM $MgCl_2$.

Further, the four DNA single strands respectively carrying AS1411 and nucleic acid drug are mixed with a mole ratio of 1:1:1:1.

Further, the volume ratio of four DNA single strands respectively carrying AS1411 and nucleic acid drug to the TM buffer is 1:1:1:1:96.

Further, the concentration of each single strand of the tetrahedral DNA nanostructure is 1 µM.

Further, the nucleic acid drug is selected from the group consisting of CpG, antisense oligonucleotide, microRNA, and siRNA.

CpG is selected from the group consisting of Class-A CpG, Class-B CpG, Class-C CpG, and Class-P CpG. More specifically, the CpG is selected from the group consisting of Class-A ODN2216, Class-A ODN2336, Class-B ODN2006, Class-C ODN2395, and Class-P ODN21798.

The antisense oligonucleotide is selected from the group consisting of ISIS 8005, ISIS 1082, ISIS 2105, ISIS 2302, ISIS 3521, ISIS 5132, ISIS 2922, ISIS 1082, ISIS 11061, ISIS 12959, and ISIS 481464.

The microRNA is selected from the group consisting of miR-34a, miR-1908, miR-302, miR-302d, miR-363, miR-137, miR-210, miR-486-5p, miR-21, miR-196a, miR-140, miR-125a-3p, miR-483-5p, miR-204-5p, miR-540, miR-146b, miR-27, miR-27b, miR-17-5p, miR-106a, miR-22, miR-30c, miR-30, miR-130, miR-138, miR-31, miR-326, miR-135, miR-26a, miR-148b, miR-218, miR-100, miR-196b, miR-92a, miR-193b, miR-194, miR-124, miR-133b, and miR-122.

The sequences of four DNA single strands of the tetrahedral DNA nanostructure are respectively as below:

S1:
(SEQ ID NO: 1)
5'-ATTTATCACCCGCCATAGTAGACGTATCACCAGGCAGTTG
AGACGAACATTCCTAAGTCTGAA-3';

S2:
(SEQ ID NO: 2)
5'-ACATGCGAGGGTCCAATACCGACGATTACAGCTTGCTAC
ACGATTCAGACTTAGGAATGTTCG-3';

S3:
(SEQ ID NO: 3)
5'-ACTACTATGGCGGGTGATAAAACGTGTAGCAAGCTGTAAT
CGACGGGAAGAGCATGCCCATCC-3';

-continued

S4:
(SEQ ID NO: 4)
5'-ACGGTATTGGACCCTCGCATGACTCAACTGCCTGGTGATA
CGAGGATGGGCATGCTCTTCCCG-3'.

TDNs-AS1411-nucleic acid drug nanocomposite based drug delivery system prepared by the above method.

TDNs-AS1411-nucleic acid drug nanocomposite based drug delivery system and the preparation method thereof provided by the present invention has the following beneficial effects:

(1) The nucleic acid aptamer AS1411 can be bound to any single strand of tetrahedral DNA nanostructure. Also, the nucleic acid drug for treating neoplastic disease can be bound to any single strand of tetrahedral DNA nanostructure. When the nucleic acid aptamer AS1411 and the nucleic acid drug respectively bind to different single strands of tetrahedral DNA nanostructure, reaction is conducted under certain conditions with the DNA single strands that do not carry AS1411 or nucleic acid drug, and then TDNs-AS1411-nucleic acid drug nanocomposite based drug delivery system is prepared.

(2) The TDNs of the TDNs-AS1411-nucleic acid drug nanocomposite based drug delivery system can enter the cells without transfection agent and deliver the nucleic acid drug into cells. Thus, the function of AS1411 is to bring drugs into nucleus to take effect on tumor cells. The drugs will not be degraded by the lysosome during shuttling in cells. The targeting specificity is good. The drug efficacy will not be lowered.

DETAILED DESCRIPTION OF THE INVENTION

Embodiment 1

A method to prepare TDNs-AS1411-nucleic acid drug nanocomposite based drug delivery system includes the following steps. AS1411 and CpG are bound to tetrahedral DNA nanostructure respectively. The tetrahedral DNA nanostructure includes four DNA single strands. The concentration of each DNA single strand is 1 µM. There is a binding site in each single strand. There are four binding sites in total. Both the AS1411 and the CpG can bind to the 5' end of each single strand (S1, S2, S3, and S4) of the tetrahedral DNA nanostructure. Effective binding ways are as follows: (1) one of the strands combines with AS1411, and the other one of three strands combine with CpG; (2) one of the strands combines with AS1411, and the other two strands combine with CpG; (3) one of the strands combines with AS1411, and the remaining three strands combine with CpG; (4) two of the strands combines with AS1411, and the other one of three strands combine with CpG; (5) two strands combine with AS1411, and the remaining two strands combine with CpG; (6) three strands combine with AS1411, and the remaining one strand combines with CpG.

Four single strands (with a molar ratio of 1:1:1:1) obtained by the binding way (1) are mixed with the TM buffer (10 mM Tris-HCl, 50 mM MgCl$_2$, pH8.0). The volume of each strand is 1 µL. The volume of the TM buffer is 96 µL. The total reaction system is 100 µL. After well mixed, the mixture is put into a PCR apparatus. The temperature is quickly raised to 95° C. and maintained for 10 min. Next, the temperature is cooled down to 4° C. and maintained for 20 min, such that the TDNs-AS1411-nucleic acid drug nanocomposite based drug delivery system is obtained.

Methods of 6% non-denaturing polyacrylamide gel electrophoresis (PAGE), dynamic light scatter (DLS), atomic force microscope (AFM), etc. can be conducted to verify whether the TDNs-AS1411-nucleic acid drug nanocomposite based drug delivery system is successfully prepared.

The sequences of the four DNA single strands are respectively as below:

S1:
(SEQ ID NO: 1)
5'-ATTTATCACCCGCCATAGTAGACGTATCACCAGGCAGTTG
AGACGAACATTCCTAAGTCTGAA-3';

S2:
(SEQ ID NO: 2)
5'-ACATGCGAGGGTCCAATACCGACGATTACAGCTTGCTAC
ACGATTCAGACTTAGGAATGTTCG-3';

S3:
(SEQ ID NO: 3)
5'-ACTACTATGGCGGGTGATAAAACGTGTAGCAAGCTGTAAT
CGACGGGAAGAGCATGCCCATCC-3';

S4:
(SEQ ID NO: 4)
5'-ACGGTATTGGACCCTCGCATGACTCAACTGCCTGGTGATA
CGAGGATGGGCATGCTCTTCCCG-3'.

AS1411 can bind to any single strand of tetrahedral DNA nanostructure at the 5' terminal of the DNA. The sequences after binding are as follows:

S1-AS1411:
(SEQ ID NO: 5)
5'-GGTGGTGGTGGTTGTGGTGGTGGTGGT-ATTTATCACCCGCCATAGT
AGACGTATCACCAGGCAGTTGAGACGAACATTCCTAAGTCTGAA-3';

S2-AS1411:
(SEQ ID NO: 6)
5'-GGTGGTGGTGGTTGTGGTGGTGGTGGT-ACATGCGAGGGTCCAATAC
CGACGATTACAGCTTGCTACACGATTCAGACTTAGGAATGTTCG-3';

S3-AS1411:
(SEQ ID NO: 7)
5'-GGTGGTGGTGGTTGTGGTGGTGGTGGT-ACTACTATGGCGGGTGATA
AAACGTGTAGCAAGCTGTAATCGACGGGAAGAGCATGCCCATCC-3';

S4-AS1411:
(SEQ ID NO: 8)
5'-GGTGGTGGTGGTTGTGGTGGTGGTGGT-ACGGTATTGGACCCTCGCA
TGACTCAACTGCCTGGTGATACGAGGATGGGCATGCTCTTCCCG-3';

CpG can also bind to any single strand of tetrahedral DNA nanostructure at the 5' terminal of the DNA. The sequences after binding are as follows:

CpG:
(SEQ ID NO: 13)
5'-TCCATGACGTTCCTGACG-3';

S1-CpG:
(SEQ ID NO: 9)
5'-TCCATGACGTTCCTGACG-ATTTATCACCCGCCATAGTAGACGTATC
ACCAGGCAGTTGAGACGAACATTCCTAAGTCTGAA-3';

S2-CpG:
(SEQ ID NO: 10)
5'-TCCATGACGTTCCTGACG-ACATGCGAGGGTCCAATACCGACGATTA
CAGCTTGCTACACGATTCAGACTTAGGAATGTTCG-3';

S3-CpG:
(SEQ ID NO: 11)
5'-TCCATGACGTTCCTGACG-ACTACTATGGCGGGTGATAAAACGTGTA
GCAAGCTGTAATCGACGGGAAGAGCATGCCCATCC-3';

-continued

S4-CpG:

(SEQ ID NO: 12)
5'-TCCATGACGTTCCTGACG-ACGGTATTGGACCCTCGCATGACTCAAC
TGCCTGGTGATACGAGGATGGGCATGCTCTTCCCG-3'.

Embodiment 2

AS1411 and CpG bind to tetrahedral DNA nanostructure in the binding way (2). Next, the combined DNA is mixed with the TM buffer. The remaining operations are the same as those in Embodiment 1.

Embodiment 3

AS1411 and CpG bind to tetrahedral DNA nanostructure in the binding way (3). Next, the combined DNA is mixed with the TM buffer. The remaining operations are the same as those in Embodiment 1.

Embodiment 4

AS1411 and CpG bind to tetrahedral DNA nanostructure in the binding way (4). Next, the combined DNA is mixed with the TM buffer. The remaining operations are the same as those in Embodiment 1.

Embodiment 5

AS1411 and CpG bind to tetrahedral DNA nanostructure in the binding way (5). Next, the combined DNA is mixed with the TM buffer. The remaining operations are the same as those in Embodiment 1.

Embodiment 6

AS1411 and CpG bind to tetrahedral DNA nanostructure in the binding way (6). Next, the combined DNA is mixed with the TM buffer. The remaining operations are the same as those in Embodiment 1.

CpG is the well-known immunostimulation nucleic acid, the main function of which is to activate immune response of cells to treat diseases including infections, tumors, and allergies, etc. AS1411 can specifically recognize the over-expressed pyrenin receptor in the cancer cell membrane. Moreover, AS1411 can be delivered into the nucleus with the mediation of the pyrenin during shuttling in cells. There are four binding sites on tetrahedral DNA nanostructure in total. That is, several different CpGs and AS1411s can be bound respectively.

(1) When one binding site connects with CpG, and one binding site connects with AS1411, the prepared drug delivery system can enter the nucleus (compared with that the tetrahedral DNA nanostructures enters the nucleus alone) and has certain immunostimulatory effect, but the effect is relatively weak.

(2) When one binding site connects with CpG, and two binding sites connect with AS1411, the prepared drug delivery system enters the nucleus with an increased amount (compared with that the tetrahedral DNA nanostructures with one AS1411 enters the nucleus), and has certain immunostimulatory effect, but the effect is still relatively weak.

(3) When one binding site connects with CpG, and the remaining three binding sites connect with AS1411, the prepared drug delivery system enters the nucleus with a significantly increased amount (compared with that the tetrahedral DNA nanostructures enters the nucleus alone). However, since only one CpG is carried, there is certain immunostimulatory effect, but not so strong.

(4) When two binding sites connect with CpG, and one binding site connects with AS1411, the prepared drug delivery system can enter the nucleus (compared with that the tetrahedral DNA nanostructures enters the nucleus alone), and has certain immunostimulatory effect, and the effect is relatively strong.

(5) When two binding sites connect with CpG, and the other two connect with AS1411, the prepared drug delivery system enters the nucleus with significantly increased amount (compared with that the tetrahedral DNA nanostructures enters the nucleus alone). The amount of entering the nucleus goes beyond that of (4). Also, the achieved immunostimulatory effect is relatively strong.

(6) When three binding sites connect with CpG, and the other one connects with AS1411, the prepared drug delivery system enters the nucleus with a lower amount than those of (4) and (5). However, the immunostimulatory effect is stronger than that of (5).

After comprehensive consideration, method (5) is chosen. Because the amount of the drug delivery system entering nucleus is large, immunostimulatory effect is strong, and functioning time in nucleus is long.

What is claimed is:

1. A method for preparing a TDNs-AS1411-nucleic acid drug nanocomposite based drug delivery system, comprising the following steps:
  binding a AS1411 and a nucleic acid drug to a tetrahedral DNA nanostructure (TDNs) respectively; wherein the AS1411 is a nucleic acid aptamer;
  selecting four DNA single strands respectively carrying the AS1411 and the nucleic acid drug;
  mixing the four DNA single strands;
  adding the DNA single strands to TM buffer;
  mixing the DNA single strands and the TM buffer uniformly;
  putting the mixture into a PCR apparatus;
  raising the temperature to 95° C. and maintaining for 10 min; and
  cooling down to 4° C. and maintaining for 20 min to obtain the TDNs-AS1411-nucleic acid drug nanocomposite based drug delivery system;
  wherein the nucleic acid drug is a CpG nucleic acid having the sequence of SEQ ID NO: 13; and the AS1411 has a nucleotide sequence of residues 1 to 27 from the 5' terminus of a S1-AS1411 having the sequence of SEQ ID NO: 5.

2. The method for preparing the TDNs-AS1411-nucleic acid drug nanocomposite based drug delivery system of claim 1, wherein the TM buffer with pH value of 8.0, includes 5-10 mM Tris-HCl and 5-50 mM $MgCl_2$.

3. The method for preparing the TDNs-AS1411-nucleic acid drug nanocomposite based drug delivery system of claim 2, wherein the TM buffer with pH value of 8.0, includes 10 mM Tris-HCl and 50 mM $MgCl_2$.

4. The method for preparing the TDNs-AS1411-nucleic acid drug nanocomposite based drug delivery system of claim 1, wherein four DNA single strands respectively carrying the AS1411 and the nucleic acid drug are mixed with a mole ratio of 1:1:1:1.

5. The method for preparing the TDNs-AS1411-nucleic acid drug nanocomposite based drug delivery system of claim 1, wherein the volume ratio of four DNA single strands respectively carrying the AS1411 and the nucleic acid drug to the TM buffer is 1:1:1:1:96.

6. The method for preparing the TDNs-AS1411-nucleic acid drug nanocomposite based drug delivery system of claim 1, wherein the concentration of each single strand of the TDNs is 1 μM.

7. A method for preparing a TDNs-AS1411-nucleic acid drug nanocomposite based drug delivery system, comprising the following steps:
  binding a AS1411 and a nucleic acid drug to a tetrahedral DNA nanostructure (TDNs) respectively; wherein the AS1411 is a nucleic acid aptamer;
  selecting four DNA single strands respectively carrying the AS1411 and the nucleic acid drug;
  mixing the four DNA single strands;
  adding the DNA single strands to TM buffer;
  mixing the DNA single strands and the TM buffer uniformly;
  putting the mixture into a PCR apparatus;
  raising the temperature to 95° C. and maintaining for 10 min; and
  cooling down to 4° C. and maintaining for 20 min to obtain the TDNs-AS1411-nucleic acid drug nanocomposite based drug delivery system;
  wherein the TDNs includes four DNA single strands having the sequences of SEQ ID NOs: 1-4, respectively.

8. The method for preparing the TDNs-AS1411-nucleic acid drug nanocomposite based drug delivery system of claim 1, wherein the four DNA single strands respectively carrying AS1411 and CpG include a first DNA single strand carrying AS1411 or CpG, having the sequence selected from SEQ ID NO: 5 or SEQ ID NO: 9, a second DNA single strand carrying AS1411 or CpG, having the sequence selected from SEQ ID NO: 6 or SEQ ID NO: 10, a third DNA single strand carrying AS1411 or CpG, having the sequence selected from SEQ ID NO: 7 or SEQ ID NO: 11, and a fourth DNA single strand carrying AS1411 or CpG, having the sequence selected from SEQ ID NO: 8 or SEQ ID NO: 12.

9. The method for preparing the TDNs-AS1411-nucleic acid drug nanocomposite based drug delivery system of claim 7, wherein the TM buffer with pH value of 8.0, includes 5-10 mM Tris-HCl and 5-50 mM $MgCl_2$.

10. The method for preparing the TDNs-AS1411-nucleic acid drug nanocomposite based drug delivery system of claim 9, wherein the TM buffer with pH value of 8.0, includes 10 mM Tris-HCl and 50 mM $MgCl_2$.

11. The method for preparing the TDNs-AS1411-nucleic acid drug nanocomposite based drug delivery system of claim 7, wherein four DNA single strands respectively carrying the AS1411 and the nucleic acid drug are mixed with a mole ratio of 1:1:1:1.

12. The method for preparing the TDNs-AS1411-nucleic acid drug nanocomposite based drug delivery system of claim 7, wherein the volume ratio of four DNA single strands respectively carrying the AS1411 and the nucleic acid drug to the TM buffer is 1:1:1:1:96.

13. The method for preparing the TDNs-AS1411-nucleic acid drug nanocomposite based drug delivery system of claim 7, wherein the concentration of each single strand of the TDNs is 1 μM.

* * * * *